(12) United States Patent
Tarentino

(10) Patent No.: US 6,605,065 B1
(45) Date of Patent: Aug. 12, 2003

(54) NON-SLIP SYRINGE

(76) Inventor: Tony Tarentino, 559 Fellsway West, Medford, MA (US) 02155

( * ) Notice: Subject to any disclaimer, the term of this patent is extended or adjusted under 35 U.S.C. 154(b) by 183 days.

(21) Appl. No.: 09/594,998

(22) Filed: Jun. 15, 2000

(51) Int. Cl.[7] ................................................ A61M 5/00
(52) U.S. Cl. ..................................................... 604/187
(58) Field of Search ................................ 604/187, 188, 604/190, 192, 193; 428/99

(56) References Cited

U.S. PATENT DOCUMENTS

| | | | | |
|---|---|---|---|---|
| 3,787,898 A | * | 1/1974 | Walker ........................... | 2/163 |
| 4,968,302 A | * | 11/1990 | Schluter et al. ............. | 604/135 |
| 4,994,046 A | * | 2/1991 | Wesson et al. .............. | 128/919 |
| 5,286,258 A | * | 2/1994 | Haber et al. ................ | 206/219 |
| 5,665,071 A | * | 9/1997 | Wyrick ......................... | 604/131 |
| 5,794,767 A | * | 8/1998 | Wilson ......................... | 206/37 |

* cited by examiner

Primary Examiner—Daniel Robinson
(74) Attorney, Agent, or Firm—Mark P. White

(57) ABSTRACT

A self-injection syringe includes an injection button, a syringe body, a needle, and a non-slip surface attached to the syringe body. The non-slip surface may be either formed into the surface of the syringe body, or may be a hook-and-eye fastener material of the Velcro type. In one version of this invention, non-slip surface is confined to a narrow strip disposed lengthwise along the syringe body, so that it falls under the fingers of the user when wrapped around the body. This invention is especially useful when the syringe is of the type in the form of a pen, which contains a cartridge of medication within a cartridge holder, with the cartridge containing enough medication for a number of injections. In this configuration, the syringe has a removable cap and pocket clip, for ease of carrying.

4 Claims, 4 Drawing Sheets

NON-SLIP SYRINGE

BACKGROUND OF THE INVENTION

1. Field of the Invention

The present invention relates to a syringe for self injection which can be handled with one hand without slipping.

2. Description Relative to the Prior Art

Millions of people in the United States alone have medical conditions which require self-injection of one or more medications on a regular basis. Diabetes, for instance, is a common disease which requires sufferers to inject themselves with insulin one or more times each day.

The prior art syringe, shown in FIG. 3, is held with the fingers of one hand, with the first and second fingers grasping the handles 12, while the thumb depresses the injection button 19. The user may or may not grasp the barrel 14 with his free hand, to guide the needle 16 into the injection site.

Recently a number of high-technology syringes have been introduced to make the process of self-injection easier to manage. Eli Lilly and Company, of Indianapolis, Ind., has introduced the "insulin pen", shown in FIG. 1, which has the outward appearance of a fountain pen, with a removable swivel cap 2, and a clip 5 to attach to a pocket. Referring to FIG. 4, when the cap is removed, the insulin pen contains an insulin cartridge 32, within a cartridge holder 34, containing enough insulin for many injections. The number of doses remaining is shown in the dose window 28. Referring to FIG. 2, the user holds the pen in one hand with his hand wrapped about the upper barrel 12, and depresses the injection button 20 with the thumb. The dose is changed by means of the dose knob 22. The notches 24, 26, are used to align the dose knob when changing the dose.

The insulin pen has one disadvantage, however: the user, when attempting to manuever the pen with one hand, finds the barrel is slippery, and therefore awkward to manage. The current invention solves this problem by means of non-slip material strategically placed.

SUMMARY OF THE INVENTION

It is an object of this invention to provide a self-injection syringe which can be easily managed with one hand.

According to one aspect of the invention, the self-injection syringe includes an injection button, a syringe body; a needle, and a non-slip surface attached to the syringe body.

According to a second aspect of the invention, the non-slip surface is formed from a hook-and-eye fastener material, attached to the body with an adhesive.

According to a third aspect of the invention, the non-slip surface is confined to a narrow strip disposed lengthwise along the syringe body.

According to a fourth aspect of the invention, the syringe body further includes a cartridge holder, and a cartridge containing enough medication for many different injections.

According to a final aspect of the invention, the syringe is in the form of a pen, which contains a removable cap and pocket clip.

BRIEF DESCRIPTION OF THE DRAWINGS

These, and further features of the invention, may be better understood with reference to the accompanying specification and drawings depicting the preferred embodiment, in which.

DESCRIPTION OF THE PREFERRED EMBODIMENTS

Figure 2:
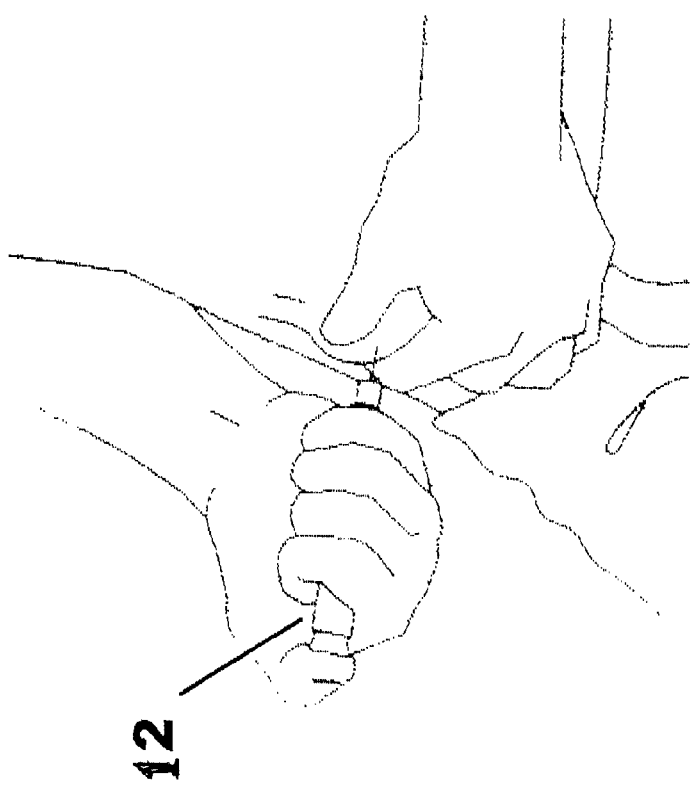
FIG. 2 depicts a user injecting himself with one hand, using an insulin pen-type syringe.

The invention may be understood by first referring to FIG. 2, which depicts a user injecting himself with a syringe 2. In this figure the user is grasping the syringe in the right hand, using the fingers to hold the body of the syringe, while depressing the injection button with the thumb of the right hand.

Using the injection technique shown in this figure, however, causes problems when the syringe surface is slippery and is not easily gripped with the fingers while pushing the injection button at the same time.

There are many reasons why a person injecting himself with a medicine, such as insulin, would want to use one hand only. The person may not have the use of the other hand. Alternatively, he may want to use the other hand to hold or prepare the area to be injected. The slippery surface of the average syringe causes a single-handed use of the syringe to be awkward and difficult. On the other hand, the average syringe does not allow for the use of two hands.

Figure 1:
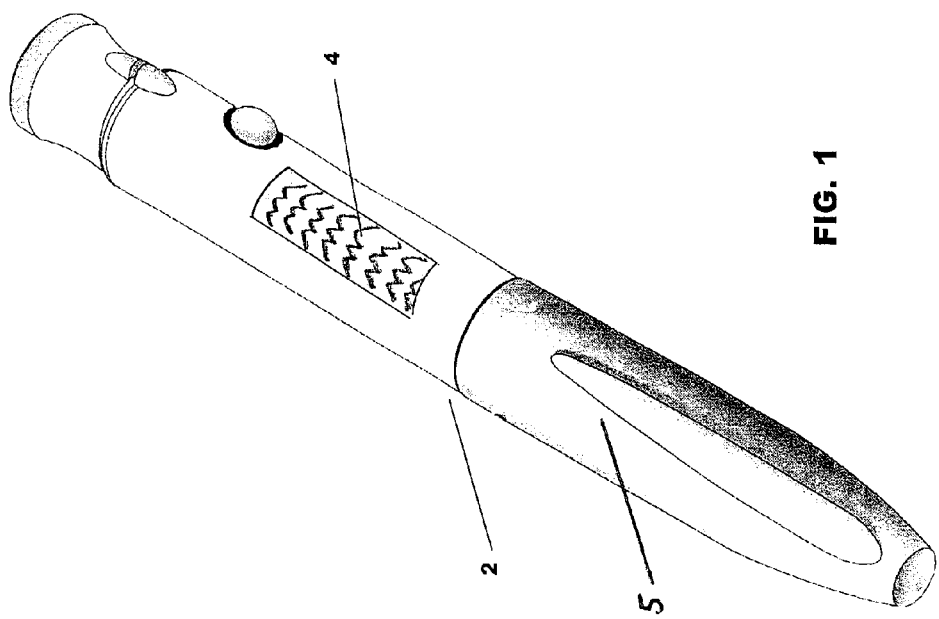
FIG. 1 depicts the insulin pen, with a strip of non-slip material attached.
Figure 4:
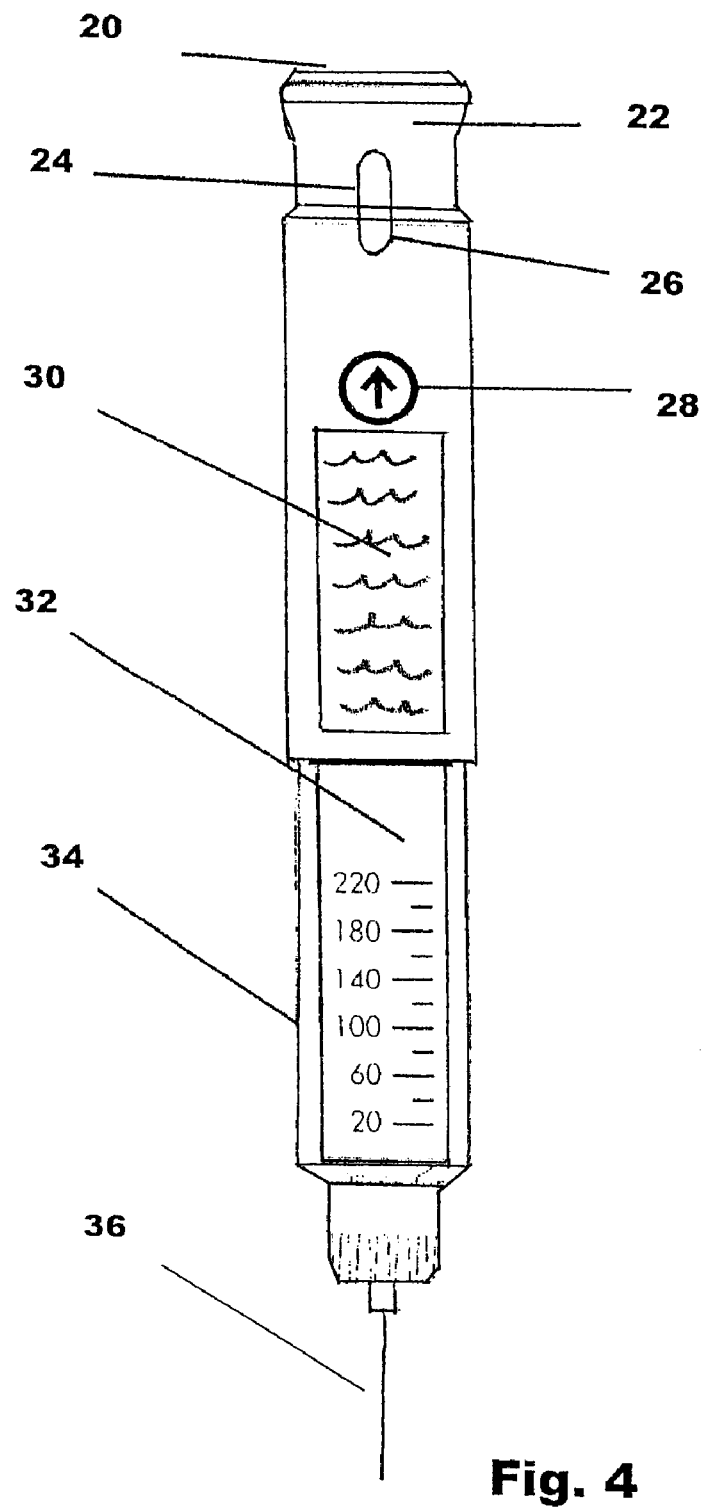
FIG. 4 depicts an insulin-needle-type syringe, with the removable cover removed, and with a non-slip strip of material attached to the body of the syringe.

This problems is solved by appending a strip of non-slip material 4 to the body of the syringe, as shown in FIG. 1. A non-slip section 30 is shown in FIG. 4 as well The material may be a strip of Velcro®, which is sold commercially in strips with adhesive on one side. Although Velcro is a hook and loop type material, in the current invention it is not used for this purpose. Either the hook side or the loop side of the material is used, since both appear to be equally efficacious in preventing sliding of the syringe. The optimum size for this strip has been found to be 1½ inches in length, by 1 inch in width, when used with the insulin pen configuration.

Figure 3:
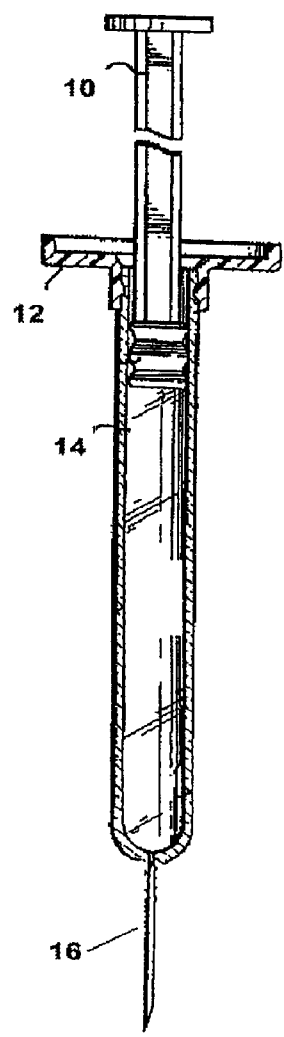
FIG. 3 depicts a prior art syringe, containing handles for grasping with the fingers, leaving the thumb free to press the injection button.

This technique may be used on many different styles of syringes, even those with handles of the traditional type shown in FIG. 3. However, the size of the non-slip strip will vary depending upon the length and diameter of the syringe body.

In any event, the non-slip material should be a strip placed in a location where it will be under the fingers of the user when wrapped around the barrel of the syringe. It has been found that having the non-slip material covering the entire surface of the barrel creates an unpleasant feeling for the user, and so the non-slip area is used only in the strip as shown in the drawings of FIGS. 1 and 4.

While the invention has been described with reference to specific embodiments, it will be apparent that improvements and modifications may be made within the purview of the invention without departing from the scope of the invention defined in the appended claims.

I claim:

1. A self-injection syringe, comprising:
   a syringe body having two ends;
   an injection button slidingly attached at one end of the body;
   a needle affixed to the other end of the body; and
   a non-slip surface attached to the syringe body wherein the non-slip surface comprises a hook-and-eye fastener material of the loop type, adhesively attached to the syringe body.

2. The syringe of claim 1, wherein the non-slip surface is confined to a narrow strip disposed lengthwise along the syringe body.

3. The syringe of claim 2, wherein the syringe body further comprises a cartridge holder contained within the body, and a cartridge within the cartridge holder containing enough medication for a multiplicity of injections.

4. The syringe of claim 3, wherein the syringe is in the form of a pen, further comprising a removable cap comprising a pocket clip, and affixed to one end of the body.

* * * * *